United States Patent [19]

Lahtinen et al.

[11] Patent Number: 5,782,880
[45] Date of Patent: Jul. 21, 1998

[54] LOW ENERGY PACING PULSE WAVEFORM FOR IMPLANTABLE PACEMAKER

[75] Inventors: Stuart P. Lahtinen, Minneapolis; Russell E. Anderson, Marine on St. Croix, both of Minn.

[73] Assignee: Medtronic, Inc., Minneapolis, Minn.

[21] Appl. No.: 636,455

[22] Filed: Apr. 23, 1996

[51] Int. Cl.$^6$ .................................................. A61N 1/362
[52] U.S. Cl. .................................................. 607/9; 607/72
[58] Field of Search .................................. 607/2, 5, 7, 9, 607/11, 68, 70, 74, 72

[56] References Cited

U.S. PATENT DOCUMENTS

| | | | |
|---|---|---|---|
| 3,885,573 | 5/1975 | Hara | 607/68 |
| 4,637,397 | 1/1987 | Jones et al. | 607/5 |
| 4,895,154 | 1/1990 | Bartelt et al. | 607/72 |
| 4,998,531 | 3/1991 | Bocchi et al. | 607/5 |

*Primary Examiner*—William E. Kamm
*Assistant Examiner*—George R. Evanisko
*Attorney, Agent, or Firm*—Harold R. Patton; Michael B. Atlass

[57] ABSTRACT

A tissue electrical stimulator and electrical pulse waveform are described. The stimulator or pulse generator may deliver the pules preferably through an endocardial electrode to pace a heart but could be used for other tissue such as nerves or to deliver defibrillation pulses through other means. A preferred circuit is described employing timing of a gate voltage level on an output transistor for the discharge capacitor(s) of the pulse generator. The waveform has a leading edge starting above zero volts and ramps upward for an initial fraction until a saturation voltage is reached and then ramps downward.

25 Claims, 7 Drawing Sheets

LOW ENERGY PACING PULSE WAVEFORM FOR IMPLANTABLE PACEMAKER

FIELD OF THE INVENTION

This invention relates to implantable cardiac pacemakers, and particularly to an improved pacing waveform and pacing output circuit for reducing energy of the waveform.

BACKGROUND OF THE INVENTION

In the history of implantable cardiac pacemakers, great strides have been made in increasing longevity, reliability, and versatility of implantable pulse generators and the associated lead systems. In the early days of implantable cardiac pacemakers, battery depletion was rapid, leading to exhaustion of the pacemaker batteries within a year from implantation.

The high energy consumption was due to a wide variety of factors, including battery self discharge, electrode-tissue interface inefficiencies, and electronic circuit current consumption. Each area of concern received considerable attention, and as improvements in one area led to increased longevity and reliability, attention was focused on the other areas. In this evolutionary process, a number of early studies were conducted to determine if the optimum pacing pulse wave shape could be found that would achieve capture of the heart at the lowest expenditure of pulse energy. Contemporaneously, however, attention was focused on other factors, particularly high energy density, low self discharge, battery technology, pacing electrode materials, sizes and configurations, variable pulse energy output pulse circuits, and capture threshold determination techniques that made dramatic improvements in IPG longevity, reliability and size. The exponential decaying voltage, pacing pulse shape achieved by a relatively simple, monophasic capacitive discharge, output circuit became accepted as the standard in pacemaker IPG technology. With the widespread adoption of multi-programmable parameters including programmable pulse width and amplitude, physicians have become accustomed to determining the patient's pacing threshold and setting the energy level to a minimum value plus an adequate safety margin. The question of whether or not an ideal pacing pulse shape to capture the heart at the least energy expenditure can be determined for an IPG has heretobefore been eclipsed by these improvements.

Meanwhile, in the field of external temporary pacemakers for pacing the heart through electrodes placed in contact with the patient's chest, effort has continued to the present time to determine a pacing pulse type and shape, including amplitude, width and wave shape, that causes the least amount of pain to the patient. In order to capture the heart through the skin and body tissue, it is necessary that the applied pacing pulse energy be several orders of magnitude higher than that necessary to capture the heart with pacing pulses applied through state of the art pacing leads in contact with the heart. In order to reduce pain to the patient, the energy is spread out in long duration, typically anodal, constant current pulses that are ramped up at the leading edge to the constant current plateau and then are ramped down at the trailing edge. Such wave shapes and pulse generating circuits are disclosed in commonly assigned U.S. Pat. No. 5,018,522 and in U.S. Pat. No. 4,349,030, for example. A precursor, rounded, square waveform is mentioned by Zoll et al. in the article "External Electrical Stimulation of the Heart", *Annals of the New York Academy of Sciences*, 932–937 (1964) and also noted by Thalen et al. in *The Artificial Cardiac Pacemaker*, pp. 211–219 at 214, (1969). Patients fitted with such external pacemakers are typically under close monitoring, and while some attention is paid to battery energy consumption, the primary focus is on reducing the energy for patient comfort while making sure that capture is not lost due to shifting of the skin electrodes or changing cardiac thresholds. The battery packs can be replaced in a few seconds to replace depleting batteries without significantly endangering the patient.

In early studies of pacing pulse shape, the article by Angelokos entitled "The Efficiency of Electrical Pulses for Cardiac Stimulation", in *Cardiologie*, 44:355–365 (1964), describes results of experiments with a number of wave shapes, particularly focusing on square waves and ascending triangular waves. The principal conclusions drawn were that regardless of the shape, the most efficient pacing pulses were the shortest, or that pulse width was more important than shape, which correlates with strength-duration analysis of the data, using electrical current values. On the other hand, Angelokos concluded that as between the two, ascending triangular waveform pulses were of greater efficiency than other tested pulses. Other studies are reported by Roy et al., in "A More Efficient Waveform for Cardiac Stimulation", in *Med. & Biol. Eng.*, vol. 9, pp. 495–501 (1971), and by Klafter in "An Optimally Energized Cardiac Pacemaker", in *IEEE Trans. Biomed. Eng.*, pp. 350–6, 1973. In both reports, it was concluded that a sawtooth waveform was more efficient than the square wave pulse waveform.

Figure 1:
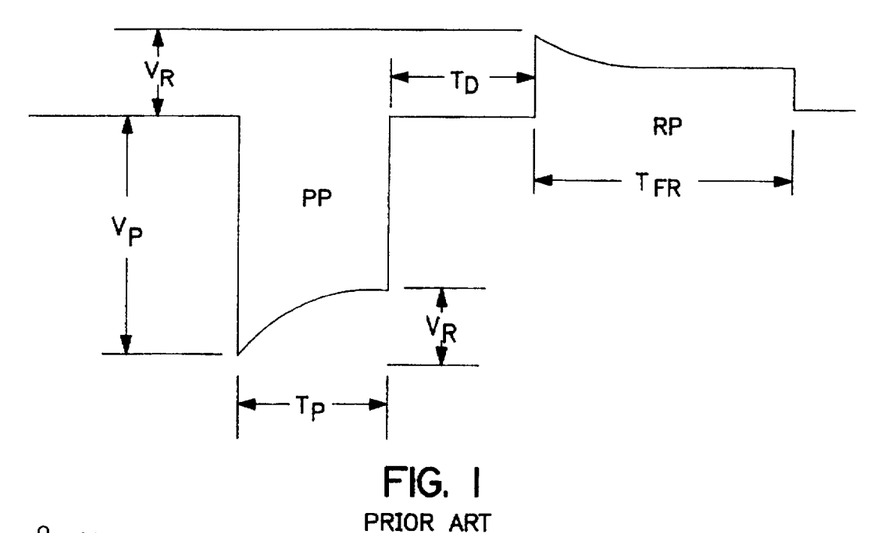
FIG. 1 is a view of a conventional prior art, implantable pacemaker, pacing pulse and recharge pulse.

Despite these conclusions, implantable pacemaker pulse generator designs continued to employ the capacitive discharge, decaying square wave voltage pulse with a sharply rising leading edge which looks more akin to the square waveform. Unlike external pacing pulse waveshapes, implantable or internally delivered pacing pulses are typically negative going or cathodal at the small surface area stimulation electrode with respect to the larger surface area return electrode. Such a typical negative going or cathodal pacing pulse PP waveshape followed by a delayed, positive going recharge pulse RP waveshape is shown in FIG. 1 which is reproduced from commonly assigned U.S. Pat. No. 4,406,286. The pacing pulse PP is produced by the exponential discharge of an output capacitor through the pacing electrodes and the impedance of the patient's heart tissue. The leading edge amplitude $V_p$ therefore falls off as the capacitor is discharged over the pulse width $T_p$ by the amount $V_R$. After a time delay $T_D$, the fast recharge voltage pulse RP is applied over the interval $T_{FR}$ to recharge the output capacitor to the voltage $V_p$. These shapes are quite unlike the sawtoothed forms described in the early studies.

A pacing output circuit for producing the pacing pulse PP and the recharge pulse RP of FIG. 1 is disclosed in detail in the '286 patent. In the '286 patent, the output capacitor 17 initially attains the voltage $V_p$ by being relatively slowly charged from source Vcc at the collector of output transistor 32 through a load resistor 28 while the output capacitor 17 is electrically connected in series with the lead electrodes 13, 14 in contact with the heart, i.e., while electrically connected in series with the heart impedance. The abrupt short rise time (in the absolute sense) of the leading edge of the pacing pulse PP is caused by the rapid switching of the output transistor 32 and a further transistor 27 which allows the cathodal discharge of output capacitor 17 through the pacing electrodes 13, 14 in a series discharge path that bypasses the load resistor 28. The rapid turn on of transistor 32 to saturation provides the abrupt leading edge, short rise time of pacing pulse PP.

Figure 2:
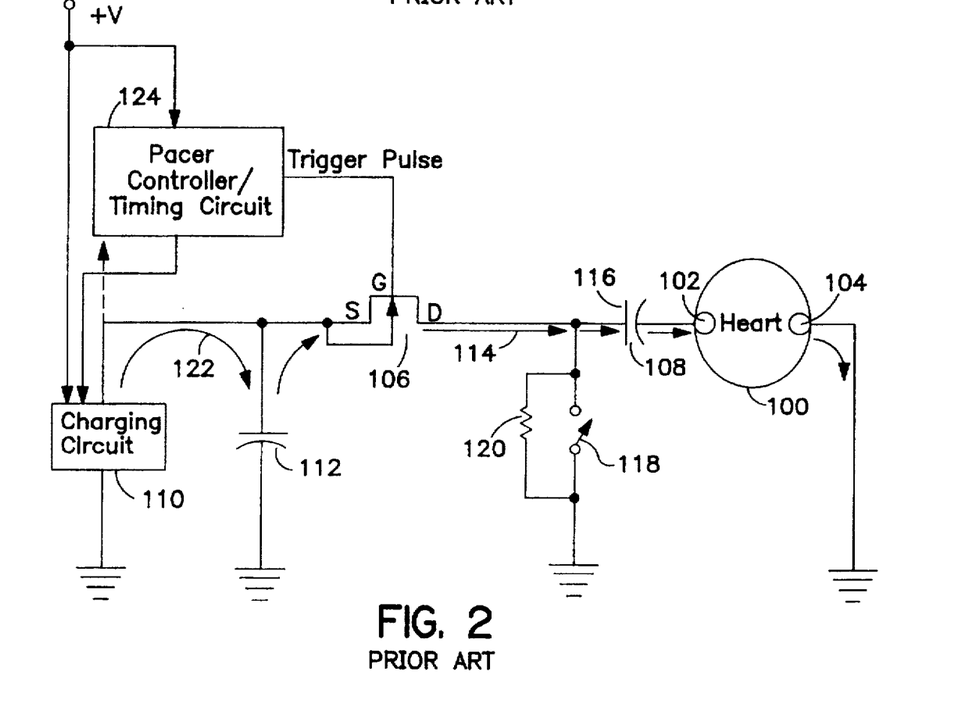
FIG. 2 is a simplified schematic block diagram of a prior art, implantable pacemaker output circuit.

Turning to FIG. 2, it depicts a simplified schematic block diagram of another typical prior art, pacemaker IPG output circuit coupled to a patient's heart 100 through pacing electrodes 102, 104 using the source-drain conduction path of a field effect transistor (FET) 106 to effect the discharge of the output capacitor 112. The output capacitor 112 is charged in a charge path 122 from the charging circuit 110 while the conduction path of FET 106 is non-conductive or open, which occurs generally during the pacing escape interval between successive pacing pulses. The charge on capacitor 112 is made negative by tying the circuit "ground" to VDD. Pacer timing and control circuit 124 defines the pacing escape interval in a manner well known in the art and supplies a pacing trigger pulse of fixed amplitude to the gate of FET 106 when a pacing pulse is to be delivered. The trigger pulse is of a predetermined pulse width defining the pacing pulse width or interval and the FET 106 responds by switching to the closed state from the open state thereby closing the source-drain discharge conduction path. The trigger pulse is of a magnitude that immediately drives the FET into saturation, and the full voltage on the output capacitor 112 is applied to the coupling capacitor 116 (also at times referred to in the prior art as the output capacitor). The pacing pulse PP, of the type shown in FIG. 1, is thereby formed by the discharge of the output capacitor 112 over the pacing pulse interval of the trigger pulse. The discharge path 114 includes the FET source-drain conduction path, coupling capacitor 116, the pacing electrode 102, the electrode-tissue interface related thereto, the heart 100 and any intervening body tissue, the pacing electrode 104 and the electrode-tissue interface related thereto, and to ground potential. The relatively high resistance of recharge resistor 120 draws little current from the pacing pulse.

A slight polarization charge is built up on capacitance in the electrode-tissue interfaces and on coupling capacitor 116. That charge is dissipated by the closing of the fast recharge switch 118 (effected by the pacer controller/timing circuit 124), during the time $T_{PR}$ of the recharge pulse RP as shown, for example, in FIG. 1. Any residual charge is dissipated through resistor 120 over the pacing escape interval.

After the pacing pulse PP is terminated by the return of the FET 106 source-drain conduction path to the open or non-conducting state, the output capacitor 112 recharges to the peak capacitor voltage through charge path 122.

The pacing output pulse PP depicted in FIG. 1 and the pace pulse generating circuits of the above-referenced '286 patent and of FIG. 2 have the advantage of being simple to provide and simple to control in pulse width and amplitude. For these and other reasons, such circuits and pulse shapes have prevailed as the output pulse shapes of choice for implantable pacemaker IPGs since the early days of cardiac pacing.

Our new waveform can be seen as a throwback to those early studies which recognized that fast rise times are not helpful to obtain tissue capture, a concept that has been discredited by IPG manufacturers for some 20 years, perhaps because of the focus on programmably variable pulse widths and amplitudes.

SUMMARY OF THE INVENTION

It is therefore an object of the present invention to provide a more efficient implantable pulse generator output pulse and circuit for providing such an output pulse so that output pulse voltage is not dissipated and implantable pacemaker battery longevity may be enhanced.

A further object is to provide a new physiologically preferred stimulation pulse waveform.

A further object is to provide for a waveform with an amplitude curve suitable for tissue stimulation that is easy to produce in current generation Implantable Pulse Generators.

In a preferred embodiment of the invention, in an implantable pulse generator for providing cardiac pacing pulses through a discharge path, including implantable pacing electrodes coupled to a patient's heart, in response to a pacing trigger pulse defining a predetermined pacing pulse interval, an improved pacing output circuit for reduced energy expenditure comprises: an output capacitor adapted to be charged in a charge path and discharged in the discharge path; charging circuit means for charging the output capacitor 7 to a predetermined peak voltage level through the charge path; and discharge circuit means operable in response to the pacing pulse trigger signal for controllably discharging the output capacitor in the discharge path and providing a pacing pulse output voltage across the pacing electrodes commencing at an initial pulse voltage level less than the predetermined peak voltage level and greater than zero and increasing over an initial fraction of the pacing pulse interval to an intermediate pulse voltage level and thereafter exponentially decreasing in voltage amplitude during a remaining fraction of the pulse interval.

Preferably, the initial pulse voltage level is in the range of approximately 10% to 50% of the predetermined peak voltage level.

Advantageously, pacing pulse energy delivered across the pacing electrodes is decreased and the residual charge of the output capacitor at the end of the pacing pulse interval is increased by restraining the discharge of the output capacitor during the initial fraction of the pacing pulse interval.

BRIEF DESCRIPTION THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 3:
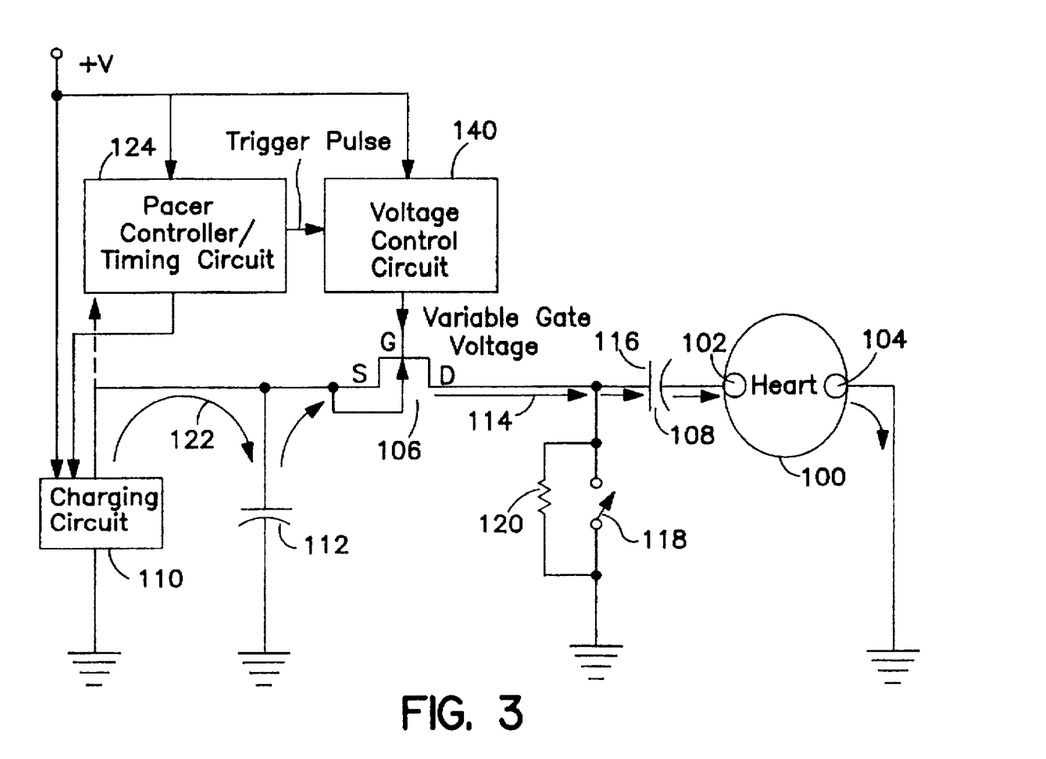
FIG. 3 is a simplified schematic block diagram of a preferred embodiment of an implantable pacemaker output circuit in accordance with the present invention.

FIG. 3 is a simplified schematic block diagram of a preferred embodiment of an implantable pacemaker output circuit in accordance with the present invention wherein a gate voltage control circuit 140 is incorporated into the output circuit and is operable in response to the pacing pulse trigger signal for providing a variable gate voltage to the gate of FET 106 during an initial fraction of the pacing pulse interval defined by the trigger pulse. The variable gate voltage renders the source-drain conduction path of the FET output transistor conductive for controllably discharging the output capacitor 112 in the discharge path 114 and providing a pacing pulse output voltage across pacing electrodes 102, 104. It will be understood that the output circuit of FIG. 3 is simplified for purposes of illustration and may be configured in other ways to provide a cathodal or other appropriate pace pulse in accord with this invention.

Figure 4:
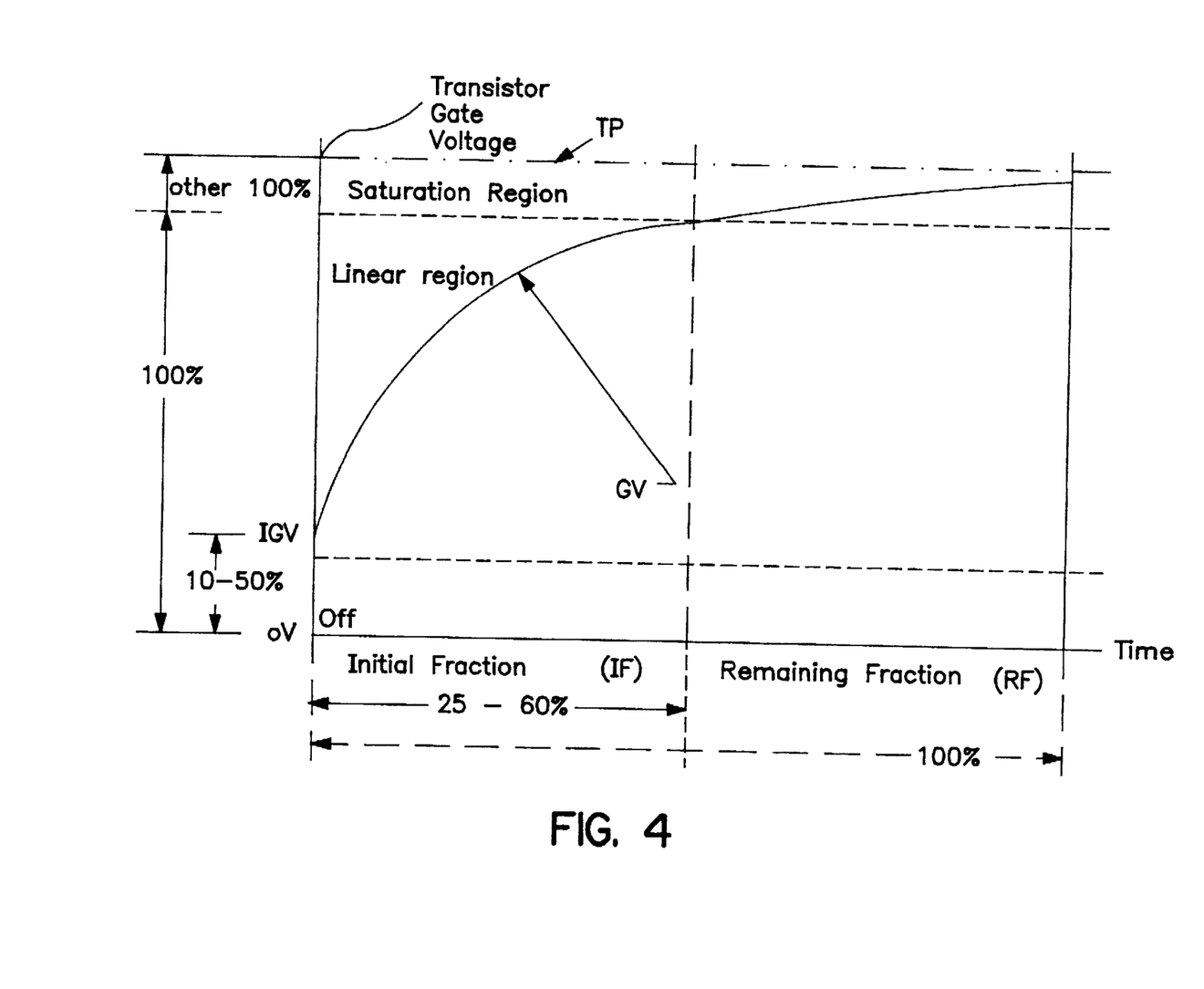
FIG. 4 is a graphical depiction of output transistor gate voltage varying over the pacing pulse width in accordance with the present invention.
Figure 5:
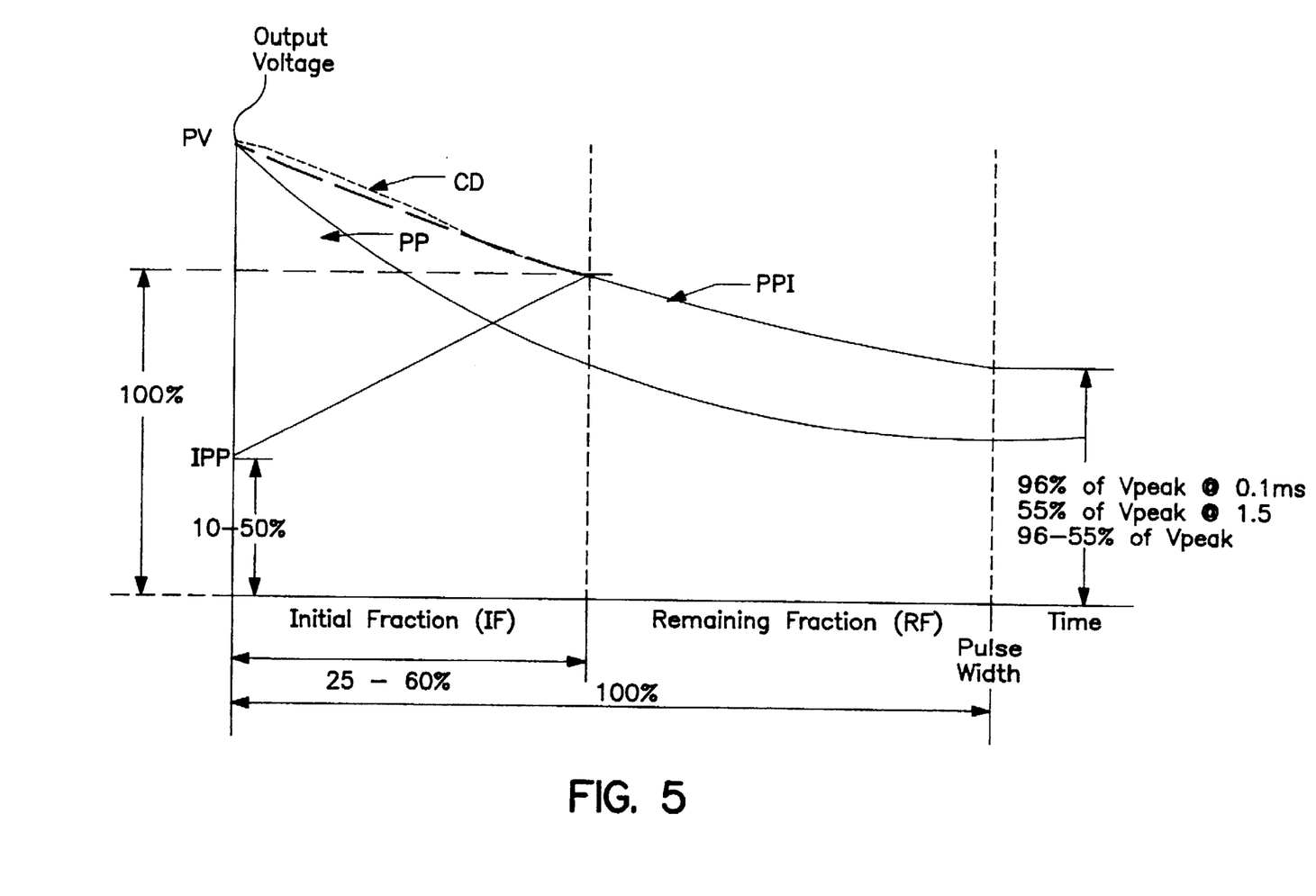
FIG. 5 is a graphical depiction of the pacing pulse voltage varying over the pacing pulse width in accordance with the present invention.

FIGS. 4 and 5, graphically depict the variable gate voltage GV varying over the pacing pulse width and the pacing pulse voltage also varying over the pacing pulse width in accordance with the present invention. This is the approximate voltage level (amplitude) to be applied as a stimulus pulse voltage, in the preferred embodiment, to the heart. FIG. 5 is the actual electrode voltage, and FIG. 4 shows the gate voltage. For convenience, the normally cathodal pacing pulse PP is shown inverted as a positive going pulse. The gate voltage control circuit provides an increasing gate voltage GV to the gate of FET 106 during an initial fraction of the pacing pulse interval defined by the pace trigger pulse TP as shown in FIG. 4. The increasing gate voltage commences at an initial gate voltage IGV sufficient to render FET 106 conductive in the linear conduction range and increases until the gate voltage GV reaches the saturation level of FET 106 thereby defining the initial fraction of the pace pulse width or interval. For comparison, the prior art trigger pulse TP is shown in FIG. 4 always within the saturation zone of the FET 106.

In accordance with the preferred embodiment of the invention, the increasing gate voltage in the linear region of conduction renders the source-drain conduction path of output FET 106 conductive in the linear operating region for discharging voltage on the output capacitor 112 in the discharge path 114. The voltage of pacing pulse PP, as viewed at coupling capacitor 116 increases from an initial pace pulse IPP voltage level that is above zero but below the peak voltage of the output capacitor 112 as shown in FIG. 5 As the pace pulse PP, voltage increases over the initial fraction, the voltage level on output capacitor 116 decreases from its peak voltage following the broken line of FIG. 5. For comparison, the prior art pacing pulse PP is also shown in FIG. 5 decreasing exponentially from the same initial peak voltage over the full pulse width but at a faster rate due to the saturation of the FET 106. When the increasing gate voltage GV reaches the saturation region amplitude shown in FIG. 4, the FET 106 is rendered fully conducting and the improved pacing pulse PP, reaches an intermediate pacing pulse voltage level corresponding to the discharge level of the linearly discharging capacitor discharge CD voltage shown in FIG. 5. Thereafter, the PP, voltage decreases exponentially in amplitude during the remaining fraction of the pacing pulse interval. In the preferred embodiments it descreases to some portion of the peak voltage before dropping to zero suddenly as the interval ends. As a result, pacing pulse energy delivered across the pacing electrodes 102, 104 is decreased, and the residual charge of the output capacitor 112 at the end of the pacing pulse interval is increased as shown in FIG. 5 by restraining the discharge of the output capacitor 112 during the initial fraction of the pacing pulse interval.

Figure 6:
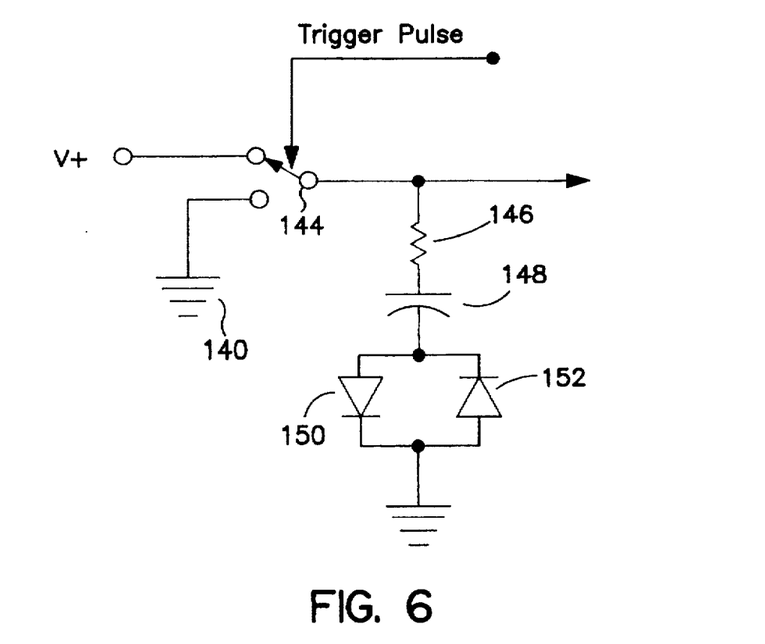
FIG. 6 is a schematic diagram of one embodiment of a gate voltage control circuit usable in the implantable pacemaker output circuit of FIG. 3.

While it is appropriate to describe a particular circuit for generating the waveform shown in FIGS. 5 and 6 to show that it can be done, it is likely that electrical engineers will avail themselves of other circuit designs to produce this waveform in the future once the energy savings provided by using it are appreciated. Accordingly, we describe the waveform with greater particularity since it is the voltage level varying throughout the waveform as shown in FIGS. 4 and 5 that provide the useful benefit of this invention. We do not intend to be limited to having claimed a circuit but do claim the inventive waveform that is used for tissue stimulation.

As can be seen in FIGS. 4 and 5, the "initial fraction" (IF) lasts for from about 25-60% of the total pulse width, and more preferably will be from 30-50%. The "remaining fraction" (RF) lasts the rest of the pulse width time. For capturing a heart chamber for example, pulse width and amplitude are varied, usually according to a formula that plots chronaxie and rheobase values, so the absolute value of the width is expected to vary in accord with the capture detection process in use by one who implements this invention. These processes are often iterative and seek a minimum energy use value for the combination of pulse width and amplitude that "captures" the stimulated chamber.

Note also that the "wave" form ends above zero volts. This also is different from the way Roy et al. and investigators of his time concluded their sawtoothed waves.

The use of our pulse waveform does not require new forms of capture detection, rather it can be used with any capture detection algorithm to find even lower energy expenditure pulses.

It is believed that this waveform may be used for stimulating other tissue besides cardiac tissue since it provides a way to deliver a lower leading edge voltage and thus allow the cells to accept the following electrical wave more easily.

Our experiments were done with dog hearts and showed the validity of our idea with respect thereto, resulting in worst case modeled energy savings of 13%. However we believe that with refinement much greater savings are possible.

Turning to FIG. 6, it is a schematic diagram of one embodiment of a gate voltage control circuit 140' usable in the implantable pacemaker output circuit of FIG. 3 depicted in a functional fashion that may be implemented in many ways in analog or digital circuitry. The switch 144 is closed by the trigger pulse from pacer controller/timing circuit 124, and current and voltage is applied from voltage source V+ to the FET 106 gate and across the series connected, resistor 146, capacitor 148 and reverse diode pair 150, 152. The current initially flows through the capacitor 148 and the forward biased diode 152 and provides the initial gate voltage IGV shown in FIG. 4. Then, as the capacitor 148 charges through the resistor 146, the variable gate voltage increases in the initial fraction as depicted in FIG. 4. The voltage builds to a maximum saturation voltage "V+", and the variable gain voltage renders the FET 106 saturated over the remaining fraction shown in FIG. 4.

Figure 7:
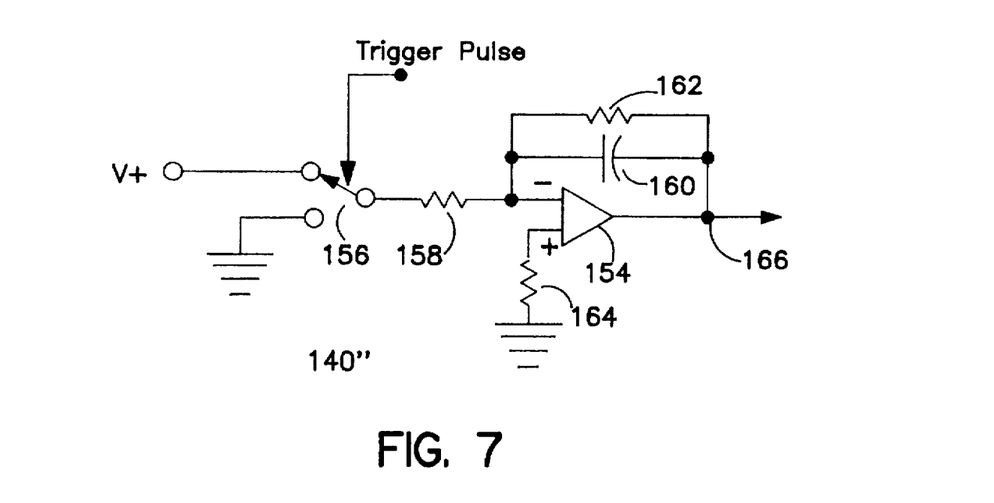
FIG. 7 is a schematic diagram of one embodiment of an alternative gate voltage control circuit usable in the implantable pacemaker output circuit of FIG. 3.

FIG. 7 is a schematic diagram of an alternative gate voltage control circuit 140" usable in the implantable pacemaker output circuit of FIG. 3 employing an operational amplifier 154 to provide the variable gate voltage to gate of FET 106 when switch 156 is closed by the trigger pulse from pacer controller/timing circuit 124. The feedback resistor 162 and capacitor 160 in conjunction with the biasing resistors 158 and 164 provide a variable gain voltage at the output 166 of operational amplifier 154 that follows the shape depicted in FIG. 4.

FIGS. 6 and 7 are but two examples of variable control circuit 140 that may be implemented in many different ways.

Figure 8:
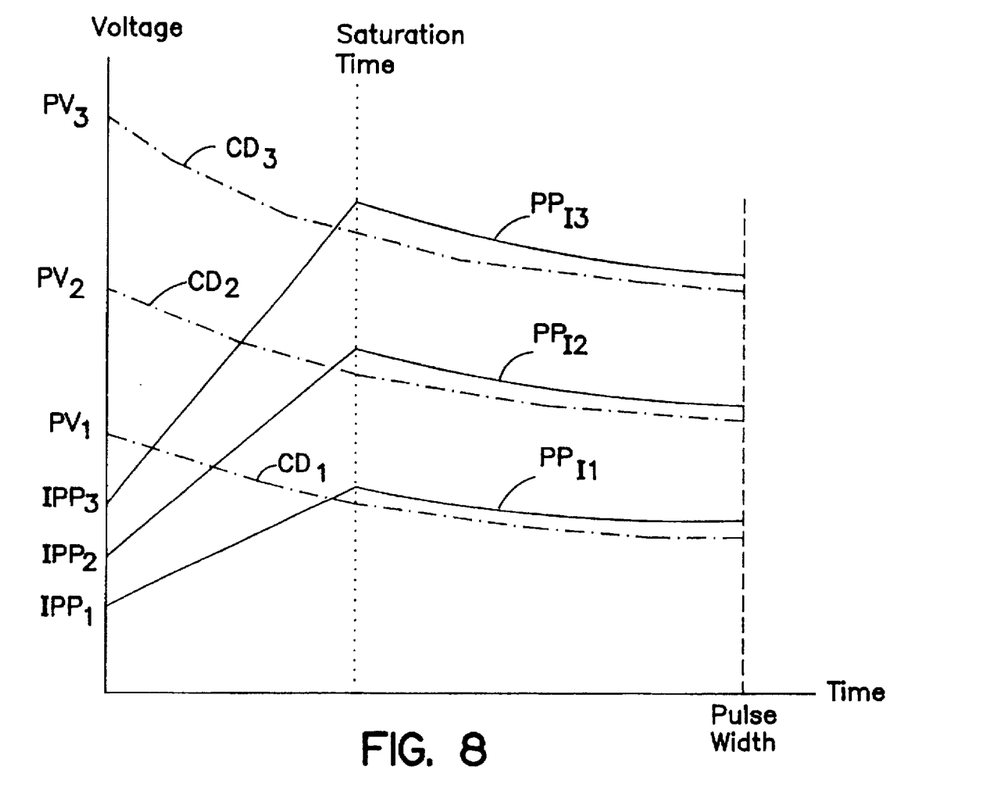
FIG. 8 is a graphical depiction of the variation of initial and remaining fractions of the pacing pulse interval with pacing pulse voltage amplitude variation in accordance with the present invention.
Figure 9:
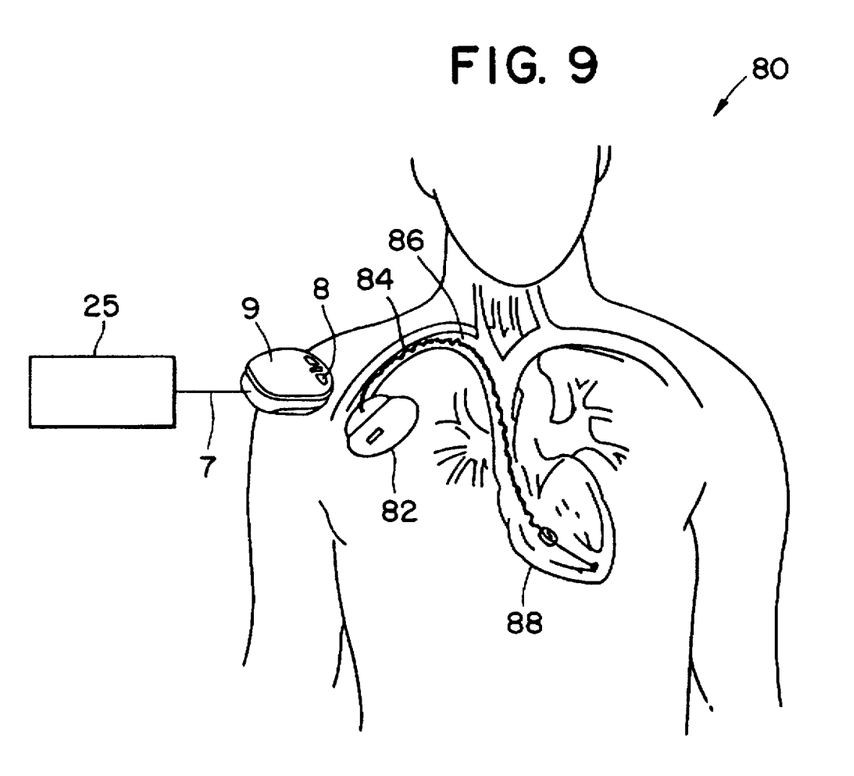
FIG. 9 is a heuristic diagram of the preferred embodiment and electrical pulse stimulation device which would use this invention in association with a human body.
Figure 10:
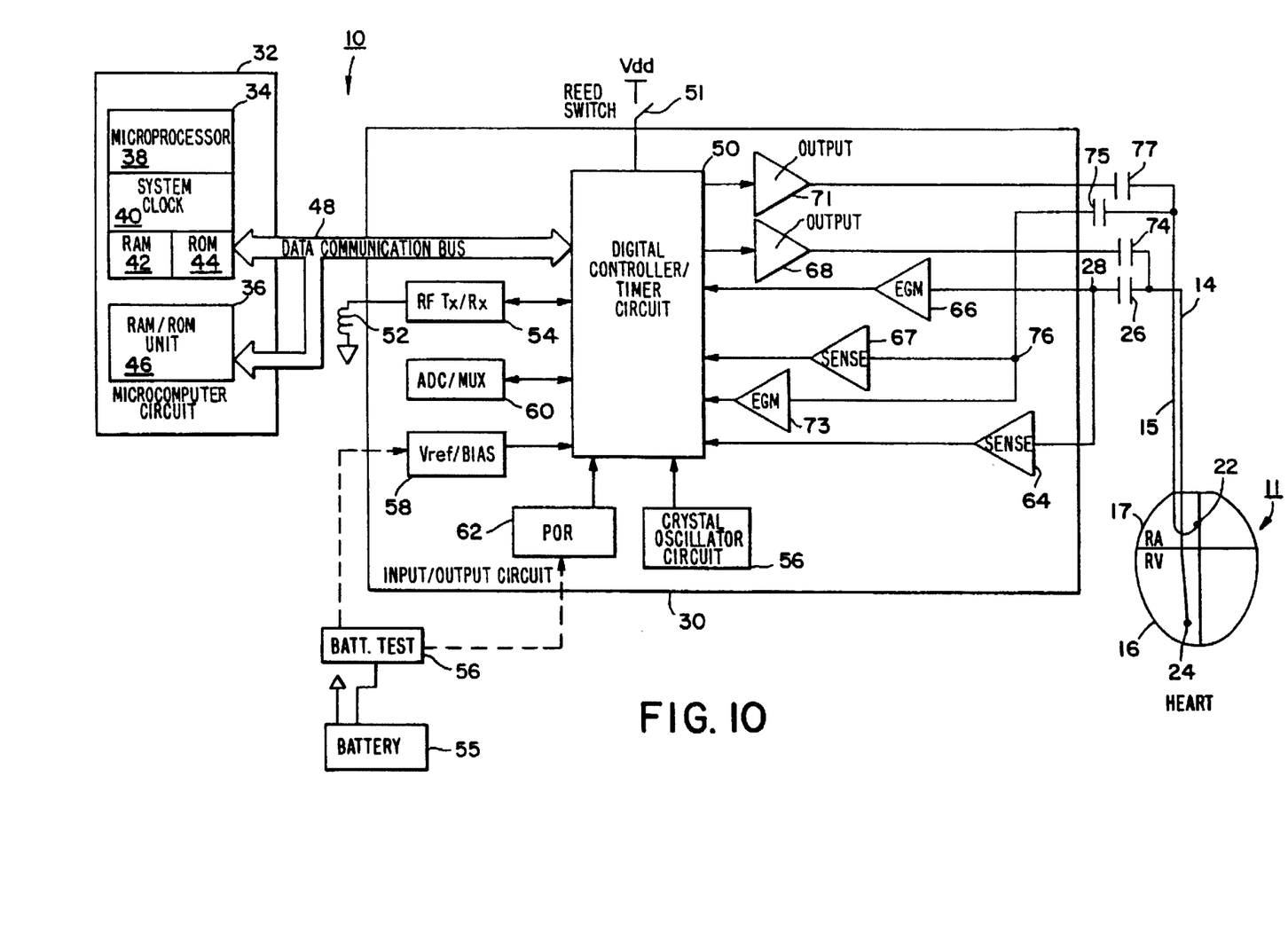
FIG. 10 is a block diagram of an implantable pulse generator that could be used with this invention.

A graphical depiction of the variation of initial and remaining fractions of the pacing pulse interval with pacing pulse voltage amplitude variation in accordance with the present invention is shown in FIG. 8. In the circuit of FIG. 3, the pacer controller/ timing circuit 124 can cause the charging circuit 110 to charge the output capacitor 112 to different peak voltages as is conventional in implantable pacemaker IPGs. In FIG. 8, three peak voltages $PV_1$, $PV_2$, $PV_3$, are shown in relation to three initial pacing pulse voltages $IPP_1$, $IPP_2$, $IPP_3$, respectively.

The improved waveforms depicted in FIGS. 5 and 8 are capable of capturing the heart or other electrically responsive tissue at the same pulse width and peak voltage PV, but expend less energy than other currently used waveforms. The energy savings prolong battery life and therefore can prolong the useful life of the pacemaker.

The waveform itself is quite different from commonly used waveforms in pacing and defibrillation pulses for stimulating heart tissue and provides the ability to save energy over them, and perhaps also better survivability. The waveforms taught here are improvements over the suggested but not accepted waveforms from studies done over 20 years ago. They provide for quick ramp up from zero volts and quick fall back to zero volts times, thus requiring very little modification to current pulse generators and allowing for continued use by current IPG's of the features that called for the currently used waveforms.

In FIG. 1 a human body 80 is fitted with an implanted medical device 82, in this example, a hermetically sealed, biocompatable, implanted pulse generator or pacemaker. For this invention any electrical tissue stimulator could use the inventive waveform, for example cardiac defibrillators and neural or muscle stimulators, but the first application for this waveform is for pacing and so that is what is detailed. The scope of the invention need not be so limited however. The pacemaker is connected to the heart 88 by a lead 84 in the subclavien vein 86 as is a common practice at the current time for implanting pacemaker devices. The programmer head 9 with hand operated switches like 8 is preferably connected by a balanced transmission wire system or cable assembly 7 to a "Programmer" or computer that is used to program pulse generators and retains information from them. Such a device as a Programmer 25 may have a keyboard and display means for communication with an attendant (not shown). Such a system is used to communicate telemetrically with the implanted device 82.

FIG. 2 is a block circuit diagram illustrating one possible form of a pacemaker 10 capable of carrying out the present invention. A detailed description of its general function follows.

Although the present invention is described in conjunction with a microprocessor-based architecture, it is understood that it could be implemented in other technology such as digital logic-based, custom integrated circuit (IC) architecture, analog circuits, etc., if desired.

Pacemakers that pace in the atrium often use two leads such as leads 14, 15. For this example embodiment other configurations could also be used as those of ordinary skill in the art will realize. Lead 14 includes an electrode 24 located near its distal end positioned within the right ventricle 16. Electrode 24 is coupled by a lead conductor 14 through an input capacitor 26 to the node 28, and to the input/output terminals of an input/output circuit 30. Lead 15 has a distal electrode positioned within the right atrium 17. Electrode 22 is coupled by a lead conductor 15 through an input capacitor 75 to a node 76, and to the input/output terminals of the Input/Output circuit 30.

Circuit 30 contains the operating input and output analog circuits for digital controlling and timing circuits to detect electrical signals derived from the heart, such as the cardiac electrogram (EGM or ECG). It may also receives output from sensors (not shown but which may be connected to the leads 14 and 15 or in the pacemaker body or connector block, etc.), and it is the part which applies stimulating pulses to the heart under the control of software-implemented algorithms in a Microcomputer Circuit 32. In this capacity it is the circuit that delivers the trigger pulse of FIGS. 3 and 6.

Microcomputer Circuit 32 is often configured as an On-Board Circuit 34 and an Off-Board Circuit 36. On-Board Circuit 34 includes a microprocessor 38, a system clock 40, and on-board RAM 42 and ROM 44. Off-Board Circuit 36 includes an off-board RAM/ROM Unit 46. Microcomputer Circuit 32 is coupled by Data Communication Bus 48 to a Digital Controller/Timer Circuit 50. Microcomputer Circuit 32 may be fabricated of custom IC devices augmented by standard RAM/ROM components or fabricated in a chip on a hybrid circuit board.

It will be understood by those skilled in the art that the electrical components represented in FIG. 2 are powered in preferred embodiments by an appropriate implantable-grade battery power source 55. A battery test circuit 56 will provide information to the controller or the microcomputer directly, in most embodiments through a Vref value circuit like 58 or a suitably configured POR circuit containing end of life indicator or other battery life/power level circuits as are well known in the art.

An antenna 52 is connected to Input/Output Circuit 30 for purposes of uplink/downlink telemetry through a radio frequency (RF) Transmitter/ Receiver Circuit (RF TX/RX) 54. Telemetering both analog and digital data between antenna 52 and an external device, such as an external "Programmer" (like the device at numeral 25 in FIG. 1) is accomplished in preferred embodiments by means such as are described in U.S. Pat. No. 5,127,404, "Telemetry Format for Implantable Medical Device", (incorporated herein by reference). Also in preferred embodiments, a reed switch 51 is connected to Input/Output Circuit 30 to enable patient follow-up by disabling sense amplifier 146 and enabling telemetry and programming functions, as is known in the art. Commonly a reed switch needs to be closed to telemeter out data but some devices will not contain reed switches, preferring to use other know devices or methods acceptable to guarantee reliability of telemetry data or initiation and against inappropriate usage.

A Crystal Oscillator Circuit 56, is preferred for providing the main timing clock signals to Digital Controller Timer Circuit 50. Most timing periods depend on a clock to turn on or off under program control, and the length of timing is generally established with reference to a number of clock cycles. A Vref/Bias Circuit 58 generates a stable voltage reference and bias currents for the analog circuits of Input/Output Circuit 30. An ADC/ Multiplexer Circuit (ADC/MUX) 60 digitizes analog signals and voltages to provide telemetry and a replacement time-indicating or end-of-life function (EOL). A Power-on-Reset Circuit (POR) 62 functions to initialize the pacemaker 10 with programmed values during power-up, and reset the program values to default states upon the detection of a low battery condition or transiently in the presence of certain undesirable conditions such as unacceptably high electromagnetic or electrical interference (EMI), for example.

The operating commands for controlling the timing of the pacemaker depicted in FIG. 2 are coupled by bus 48 to Digital Controller/Timer Circuit 50 wherein digital timers set the overall escape interval of the pacemaker and may have separate atrial and ventricular escape intervals, as well as various refractory (PVARP), blanking (PVAB) and other timing windows for controlling the operation of the peripheral components within Input/Output Circuit 50.

Digital Controller/Timer Circuit 50 is coupled to sense amplifiers (SENSE) 64 and 67, and to electrogram (EGM) amplifiers 66 and 73 for receiving amplified and processed signals picked up from electrode 24 through lead 14 and capacitor 26, and for receiving amplified and processed signals picked up from electrode 22 through lead 15 and capacitor 75, representative of the electrical activity of the patient's ventricle 16 and atrium 17, respectively. Similarly, SENSE amplifiers 64 and 67 produce sense event signals for re-setting the escape interval timer within Circuit 50. The electrogram signal developed by EGM amplifier 66 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", incorporated herein by reference.

Output pulse generators 68 and 71 provide the pacing stimuli to the patient's heart 11 through output capacitors 74 and 77 and leads 14 and 15 in response to paced trigger signals developed by Digital Controller/Timer Circuit 50 each time the escape interval times out, or an externally transmitted pacing command has been received, or in response to other stored commands as is well known in the pacing art.

In a preferred embodiment of the present invention, pacemaker 10 is capable of operating in various non-rate-responsive modes which include DDD, DDI, VVI, VOO and VVT, as well as corresponding rate-responsive modes of DDDR, DDIR, VVIR, VOOR and VVTR as well as the A (atrial) analogs of these: AAI/R, AAT/R, AOO/R, et cetera. Further, pacemaker 10 can be programmably configured to operate such that it varies its rate only in response to one selected sensor output, or in response to both sensor outputs, if desired. Many other features and functions of pacemakers as well as other electrical pulse generators may be incorporated without going beyond the scope of this invention.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

What is claimed is:

1. In an implantable pulse generator for providing cardiac pacing pulses through a discharge path including implantable pacing electrodes coupled to a patient's heart in response to a pacing pulse trigger signal defining a predetermined pacing pulse interval, an improved pacing output circuit for reduced energy expenditure comprising:

an output capacitor adapted to be charged in a charge path and discharged in said discharge path;

charging circuit means for charging said output capacitor to a predetermined peak voltage level through said charge path; and discharge circuit means operable in response to said pacing pulse trigger signal for controllably discharging said output capacitor in said discharge path and providing a pacing pulse output voltage across said implantable pacing electrodes commencing at an initial pulse voltage level less than said predetermined peak voltage level and greater than zero and increasing over an initial fraction of said pacing pulse interval to an intermediate pulse voltage level and thereafter exponentially decreasing in voltage amplitude during a remaining fraction of said pulse interval until a terminal end thereof, whereby pacing pulse energy delivered across said pacing electrodes is decreased and a residual charge of said output capacitor at the end of the pacing pulse interval is increased by restraining the discharge of said output capacitor during said initial fraction of said pacing pulse interval.

2. The implantable pulse generator of claim 1 wherein said initial pulse voltage level is in the range of approximately 10% to 50% of the predetermined peak voltage level.

3. The implantable pulse generator of claim 2 wherein said intermediate pulse voltage level corresponds to an exponential discharge level of said output capacitor reached during its discharge in the initial fraction of the pacing pulse interval.

4. The implantable pulse generator of claim 3 wherein said exponential decreasing pacing pulse output voltage corresponds to the exponential discharge of said output capacitor through an impedance across said pacing electrodes.

5. The implantable pulse generator of claim 1 wherein said intermediate pulse voltage level corresponds to a linear discharge level of said output capacitor reached during its discharge in the initial fraction of the pacing pulse interval.

6. The implantable pulse generator of claim 5 wherein a linearly decreasing pacing pulse output voltage corresponds to the linear discharge of said output capacitor through the impedance across said pacing electrodes.

7. In an implantable pulse generator for providing cardiac pacing pulses through a discharge path including an implantable pacing electrode coupled to a patient's heart in response to a pacing pulse trigger signal defining a predetermined pacing pulse interval, an improved pacing output circuit for reduced energy expenditure comprising:

output capacitor means adapted to be charged in a charge path and discharged in said discharge path;

charging circuit means for charging said output capacitor means to a predetermined peak voltage level through said charge path;

an output circuit means having a conduction path in said discharge path coupled to said output capacitor and having a control gate; and discharge voltage control circuit means operable in response to said pulse trigger signal and coupled to said control gate for providing a variable gate voltage to render said conduction path of said output circuit means conductive for controllably discharging said output capacitor means in said discharge path and providing a pacing pulse output voltage across said implantable pacing electrode(s) commencing at an initial pacing pulse voltage level less than said predetermined peak voltage level and greater than zero and increasing over an initial fraction of said pacing pulse interval to an intermediate pacing pulse voltage level and thereafter decreasing exponentially in voltage amplitude during a remaining fraction of said pulse interval until a terminal end thereof, whereby pacing pulse energy delivered across said pacing electrodes is decreased and a residual charge of said output capacitor at the end of the pacing pulse interval is increased by restraining the discharge of said output capacitor during said initial fraction of said pacing pulse interval.

8. The implantable pulse generator of claim 7 wherein said discharge voltage control circuit means further comprises:

gate voltage control means for providing an increasing gate voltage to said gate during said initial fraction rendering said conduction path of said output transistor conductive in a linear operating region for discharging said output capacitor in said discharge path at an increasing rate and providing said pacing pulse output voltage commencing from said initial pacing pulse voltage level until the increasing gate voltage renders said conduction path of said output transistor conductive in saturation for said remaining fraction of said pacing pulse interval, thereby providing said pacing pulse output voltage with an increasing voltage over said initial fraction and an exponentially decreasing voltage over said remaining fraction of said pacing pulse interval.

9. The pacing output pulse circuit of claim 8, wherein said gate voltage control means further comprises:

a diode circuit coupled to said gate for applying a fixed gate voltage to said gate for initially rendering said control circuit conductive in said linear operating region and providing said initial pacing pulse voltage level in response to said trigger pulse; and a capacitive charging circuit coupled with said diode circuit and said gate and responsive to said trigger pulse for providing an increasing gate voltage as said variable control signal over said first fraction of said pacing pulse interval until said capacitive charging circuit is charged to a saturation gate voltage level, whereby said transistor is conductive in saturation.

10. The pacing output circuit of claim 7, wherein:

said output transistor further comprises a field effect transistor having said gate and a source-drain conduction path coupled in electrical series with said output capacitor and said pacing electrodes; and said discharge voltage control circuit means is responsive to said trigger signal for providing a variable gate voltage to said gate over said initial fraction for operating said field effect transistor in a generally linearly increasing conduction range and for providing a fixed gate voltage to said gate over said subsequent fraction for operating said field effect transistor at saturation to allow exponential discharge of said output capacitor charge voltage therethrough.

11. The pacing output pulse circuit of claim 10, wherein said gate voltage control means further comprises:

a diode circuit coupled to said field effect transistor gate for applying a fixed gate voltage to said gate for initially rendering said field effect transistor conductive in said linear operating region and providing said initial pacing pulse voltage level in response to said trigger pulse; and a capacitive charging circuit coupled with said diode circuit and said field effect transistor gate and responsive to said trigger pulse for providing an increasing gate voltage as said variable control signal over said first fraction of said pacing pulse interval until said capacitive charging circuit is charged to a saturation gate voltage level, whereby said field effect transistor is conductive in saturation.

12. The implantable pulse generator of claim 7 wherein said initial pacing pulse voltage level is in a range of approximately 10% to 50% of the predetermined peak voltage level.

13. The implantable pulse generator of claim 12 wherein said intermediate pacing pulse voltage level corresponds to a linear discharge level of said output capacitor reached during its discharge in the initial fraction of the pacing pulse interval.

14. The implantable pulse generator of claim 13 wherein said linear discharge of said pacing pulse output voltage is the linear discharge of said output capacitor through the transistor conduction path and an impendance across said pacing electrodes.

15. The implantable pulse generator of claim 7 wherein said intermediate pacing pulse voltage level corresponds to an linear discharge level of said output capacitor reached during its discharge in the initial fraction of the pacing pulse interval.

16. The implantable pulse generator of claim 15 wherein said linear discharge of said pacing pulse output voltage is the linear discharge of said output capacitor through the transistor conduction path and an impendance across said pacing electrodes.

17. In an implantable pulse generator for providing cardiac pacing pulses through implantable pacing electrodes to a patient's heart and across an electrode-tissue interface and impedance of a discharge path through the patient's heart in response to a pacing pulse trigger signal having a predetermined pulse width, an improved pacing output circuit for reducing energy expenditure comprising:

an output capacitor adapted to be charged in a charge path and discharged in said discharge path to provide said pacing pulse over said pulse width;

discharge switch means having a conduction path in a discharge circuit with said output capacitor and said pacing electrodes having an open state for blocking discharge current flow and an variable closed state for allowing variable current flow in dependence on a switch control signal;

charge circuit means for charging said output capacitor to a predetermined charge voltage level while said discharge switch means is in said open state; and discharge circuit means operable in response to said pacing pulse trigger signal for providing a variable control signal to said discharge switch means for partially closing said discharge switch means and discharging said output capacitor at a progressively increasing voltage commencing from an initial pacing pulse voltage level less than said predetermined charge voltage level and greater than zero over an initial fraction of said pacing pulse interval until said discharge switch means is fully closed and thereafter allowing exponential discharge of said output capacitor voltage for a remaining fraction of said pacing pulse interval through said discharge switch.

18. The pacing output pulse circuit of claim 17, wherein said discharge switch means is a field effect transistor having a gate and a source-drain path providing said conduction path, and said discharge circuit means comprises:

gate voltage control means for providing a variable gate voltage to said gate over said first fraction for operating said field effect transistor in a generally linearly increasing conduction range and for providing a fixed gate voltage to said gate over said second fraction for operating said field effect transistor in saturation to allow exponential discharge of said output capacitor charge voltage therethrough.

19. The pacing output pulse circuit of claim 18, wherein said gate voltage control means further comprises:

a diode circuit coupled to said field effect transistor gate for applying a fixed gate voltage to said gate for initially rendering said field effect transistor conductive in said linear operating region and providing said initial pacing pulse voltage level in response to said trigger pulse; and a capacitive charging circuit coupled with said diode circuit and said field effect transistor gate and responsive to said trigger pulse for providing an increasing gate voltage as said variable control signal over said first fraction of said pacing pulse interval until said capacitive charging circuit is charged to a saturation gate voltage level, whereby said field effect transistor is conductive in saturation.

20. The implantable pulse generator of claim 17 wherein said discharge switch means is an output transistor having a gate and said conduction path, and said discharge circuit means comprises:

gate voltage control means for providing a variable gate voltage to said gate over said first fraction for operating said transistor conduction path in a generally linearly increasing conduction range and for providing a fixed gate voltage to said gate over said second fraction for operating said transistor in saturation to allow exponential discharge of said output capacitor charge voltage through said conduction path, thereby providing said pacing pulse output voltage with an increasing voltage over said initial fraction and an exponentially decreasing voltage over said remaining fraction of said pacing pulse interval.

21. The pacing output pulse circuit of claim 20, wherein said gate voltage control means further comprises:

a diode circuit coupled to said gate for applying a fixed gate voltage to said gate for initially rendering said transistor conductive in said linear operating region and providing said initial pacing pulse voltage level in response to said trigger pulse; and a capacitive charging circuit coupled with said diode circuit and said gate and responsive to said trigger pulse for providing an increasing gate voltage as said variable control signal over said first fraction of said pacing pulse interval until said capacitive charging circuit is charged to a saturation gate voltage level, whereby said transistor is conductive in saturation.

22. In a tissue stimulator having a timing means for timing a pulse interval and pulse generator means for providing a tissue stimulation pulse, the improvement comprising a pulse generator means configured for providing said tissue stimulation pulse such that when provided, said stimulation pulse has a voltage pulse waveform commencing at an initial pulse voltage level greater, in absolute value, than zero and increasing over an initial fraction of said pulse interval to an intermediate pulse voltage level and immediately thereafter exponentially decreasing in voltage amplitude from the intermediate pulse voltage level during a remaining fraction of said pulse interval.

23. The tissue stimulator of claim 22 wherein said voltage pulse waveform has a terminal end point following said remaining fraction characterized by having a terminal pulse voltage level greater, in absolute value, than zero.

24. In an implantable cardiac pacemaker having timing means for timing a pulse interval and pulse generator means for providing a pacing pulse, the improvement in said pulse generator means comprising circuit means for providing as said pacing pulse a voltage pulse waveform commencing at an initial pulse voltage level greater, in absolute value, than zero and increasing over an initial fraction of said pulse interval to an intermediate pulse voltage level and thereafter exponentially decreasing in voltage amplitude during a remaining faction of said pulse interval.

25. The pacemaker of claim 24 wherein said voltage pulse waveform has a terminal end point following said remaining fraction characterized by having a terminal pulse voltage level greater, in absolute value, than zero.

* * * * *